United States Patent [19]

Chew et al.

[11] Patent Number: 5,678,569
[45] Date of Patent: Oct. 21, 1997

[54] SURGICAL SPONGE AND NEEDLE ELECTRONIC DISPLAY AND COUNTER

[76] Inventors: Stephen Yee Kang Chew, 1439 Alewa Dr., Honolulu, Hi. 96817; Christopher Yee Chian Chew, 63 Belmont Rd., Singapore 1026, Singapore

[21] Appl. No.: 392,216

[22] Filed: Feb. 22, 1995

[51] Int. Cl.$^6$ ................................................ A61B 19/00
[52] U.S. Cl. ................................ 128/897; 604/317
[58] Field of Search ............... 128/897–98; 604/317, 604/318; 364/700, 709.01, 709.12, 710.01, 715.01

[56] References Cited

U.S. PATENT DOCUMENTS 5,443,082   8/1995   Mewburn ............................ 128/897

FOREIGN PATENT DOCUMENTS 2030739   6/1991   Canada ............................ 128/897
4017767   8/1994   WIPO ............................. 128/898

*Primary Examiner*—John P. Lacyk
*Attorney, Agent, or Firm*—John P. Halvonik

[57] ABSTRACT

An input and output display calculator for tracking medical devices used during surgery. Input buttons corresponding to the numbers and packages of needles and sponges allow the user to input this information into the calculator. Output provide for an up to date readout of the total number of such sponges/needles used during the procedure as well as a total of those that have not yet been accounted for. Input buttons on the display face of the calculator provide a means for the nurse or other personnel to input the number of needles/sponges used in increments corresponding to the number of such needles and sponges found in a typical package of such items. Subtraction buttons allow for such numbers to be removed from the display in the event of errors. A timer means records the time that such numbers are added and subtracted and a printer allows for a printed record of such to be made. Display outputs present the total number of needles/sponges used as well as the number of packages of such that have been used so far in the procedure.

14 Claims, 3 Drawing Sheets

FIG. 1

SAMPLE OF PRINTER OUTPUT

```
10:11   remove 40 needles
10:01   +8 needles
 9:56   +5 needles
 9:48   +5 laps
 9:45   -2 needles
 9:44   +2 needles
 9:35   +10 r/o
 9:31   +4 needles
 9:07   +1 needle
 8:59   +10 peanuts
 8:42   +5 needles
 8:41   -1 needle
 8:40   +1 needle
 7:52   +20 needles

DATE:  7-1-94

STICK
    NAME
    LABEL
    HERE
```

FIG.3

SURGICAL SPONGE AND NEEDLE ELECTRONIC DISPLAY AND COUNTER

BACKGROUND AND FIELD OF THE INVENTION

Suture needles used during surgery have specialized purposes and come in different packages. Suture needles used in heart valve replacement come in packages of 20. Suture needles for bowel anastomosis come in packages of 8 or 5. Needles for vascular anastomosis come in twos. Other needles come in packs of 4, 3 or singles. During major surgery various different packages will be used. During a long and complicated surgical procedure it is not unusual to use one to two hundred needles from various packages.

When a suture package is put on the surgical field (the are in and around the patient) the circulating nurse must keep a record of that package and a running total of needles on the field. This is at present done manually by recording the packages and needle count on a writing board.

Towards the end of surgery a physical count of each needle on the field is taken. The number of needles on the field must match the number on the tally board. If the numbers do not match a recount is done. It is helpful during a recount to reconcile the number of packages on the field with the number of packages written on the tally board. If the count still does not match a thorough search of the missing needle (s) is begun. A X-Ray of the patient will have to be taken if the needle count is incorrect.

It takes several seconds for the circulating nurse to record the suture packages and total the needle count. The nurse has to pick up the pen, write the number of needles in the package, and perform an arithmetic task. This method of tallying the needles is prone to arithmetic errors because of the odd-even combinations of 20, 8, 5, 4, 3, 2, and 1. This is especially so if the circulating nurse is busy and has several tasks at hand. The nurse may put off recording till later and forget about it. In addition because most nurses do a running total it is difficult to see at a glance from the tally board what different needle packages are on the field.

To reduce the number of needles on the field the scrub nurse may elect to remove used needles from the field. Used needles are kept in numbered sections of foam or magnets. These are a derivative of an invention by Thrun (U.S. Pat. No. 4,243,140). Suture boxes may contain 20 or 40+ needles when full. When removed from the field the circulating nurse has to subtract that number from the tally board.

Often times a discrepancy in needle count is not due to a retained needle inside the patient's body but due to an arithmetic error on the tally board or the circulating nurse forgetting to mark a package down.

Surgical sponges come in packages of 5 and 10. Laparotomy sponges measure 18" by 18" and are packaged in 5's. Surgical gauzes measure 4" by 4" and are packaged in 10's. Miniscule sponges called "peanuts" are packaged in 5's. Flat sponges called "cottonoids" are packaged in 10's.

During a surgical procedure various sponge packages may be used. Like suture needles, every sponge must be physically accounted for before the end of surgery. Sponges are totalled separately for each type of sponge. They are not commingled and totalled like needles. Although 5 and 10 are numbers easier to add, subtract and multiply arithmetical errors in recording during surgery do occur. Like suture needles the circulating nurse has to manually record the sponge package on the writing board when it is handed to the scrub nurse.

The present invention will save the circulating nurse time in recording the packages and eliminate arithmetic errors. All the circulating nurse has to do is to press the buttom corresponding to the number of needles or sponges in the package. The calculator advances the needle or sponge count accordingly and displays the number in a bold and bright LED display visible even in the dark. One feature of the calculator allows the circulating nurse to subtract needles from the field when a suture box is full. Another feature of the calculator is the incorporation of a small printer which makes a hard copy record on paper roll of every needle and sponge package used and the time that package was entered in the calculator. Another feature of the calculator is an audible confimation that will sound when a button is actuated.

DESCRIPTION OF THE PRIOR ART

There are no devices of which applicant is aware of that provide a running total of the number of packages as well as individual medical items used during a procedure. Nor are there any that applicant is aware of that allow the input of the number of packages as well as the number of individual needles and sponges. It is also believed that such a sponge and needle calculator having a means for displaying both the total number of needles/sponges used, as well as the total number of those that have not yet been accounted for, is also novel. Again the use of an audible sound to signify confirmation of such final and intermediate totals is also believed to be novel.

SUMMARY OF THE INVENTION

An input and output display calculator with input buttons corresponding to the numbers of individual needles and sponges as well as the number of packages of needles and sponges used during a procudure. A visual display on the face of the calculator provides for a current readout of the total number of such sponges and/or needles, both individual sponges and/or needles and packages of such used during the procedure. The visual display also has separate tally for those individual sponges and needles that have not yet been accounted for and remain in the operating area.

Input buttons on the display face of the calculator provide a means for the nurse or other personnel to input the number of needles/sponges used in increments corresponding to the number of such needles and sponges found in a typical package of such items. E.g. if a package containing five laparotomy sponges is brought into the area, the nurse will activate a button or other input means on the face of the calculator that corresponds to the five laparotomy sponges and the visual display will reflect that both 1 package and 5 total laparotomy sponges are in the operating field.

Other input buttons (subtraction buttons) allow for such number of packages and the total number of sponges/needles to be subtracted from the various visual output displays in the event of errors or when such sponges and needles may be removed. A timer means records the time that such data is input and a printer then allows for a printed record of such inputs by time. Display outputs present the total number of needles/sponges used as well as the number of packages of such that have been used so far in the procedure. Other display means provide a display of the total numbers of such that remain in the surgical area. Subtraction buttons allow for the operator to decrease the total number of such sponges/needles that remain as those sponges/needles are removed from the surgical area.

One of the primary aims of this invention is to eliminate errors in arithmetic in determing the number of needles and sponges left in the area of the patient. Also the invention creates a visual display of this information of suture and sponge packages used during surgery, thereby minimizing costly overruns in operating room and anesthesia time. More specifically, the invention will:

Minimize the time the circulating nurse takes to record the number of suture and sponge packages on the surgical field by eliminating the need to pick up a pen and write down the information. Recording and calculation now take place immediately with the press of a button.

Eliminate arithmetic errors when accounting for suture needles and surgical sponges during surgery.

Improve the display showing which suture packages and sponge packages are used during surgery, so that when a needle/sponge recount is done before the close of surgery any discrepancy in the surgical field and tally board is quickly noted.

Obtain a hardcopy printout of each suture and sponge package used during and the time the package was put on the field.

Providing audible as well as tactile confirmation when a entry is made in the calculator.

It is an object of the invention to provide a calculator that can readily display the total number of needles/sponges that have been used so far in an operation without having to resort to manual methods that would slow down such procedure.

Another object is to minimize the time spent by hospital personnel in counting the numbers of needles and sponges used during an operation and to eliminate errors of math that may occur by using manual methods.

Another object is provide a calculator that can display the total number of packages as well as individual needles/ sponges used during an operation.

Another objective is to provide a calculator that can display both the total number of needles used as well as the total number of such that remain in the operation area.

Other objectives will be apparent to those skilled in the art once the invention is shown and described.

DESCRIPTION OF THE DRAWINGS

FIG. 1 Front view of invention

FIG. 3 Sample printout from the calculator

DESCRIPTION OF THE PREFERRED EMBODIMENT

Figure 1:
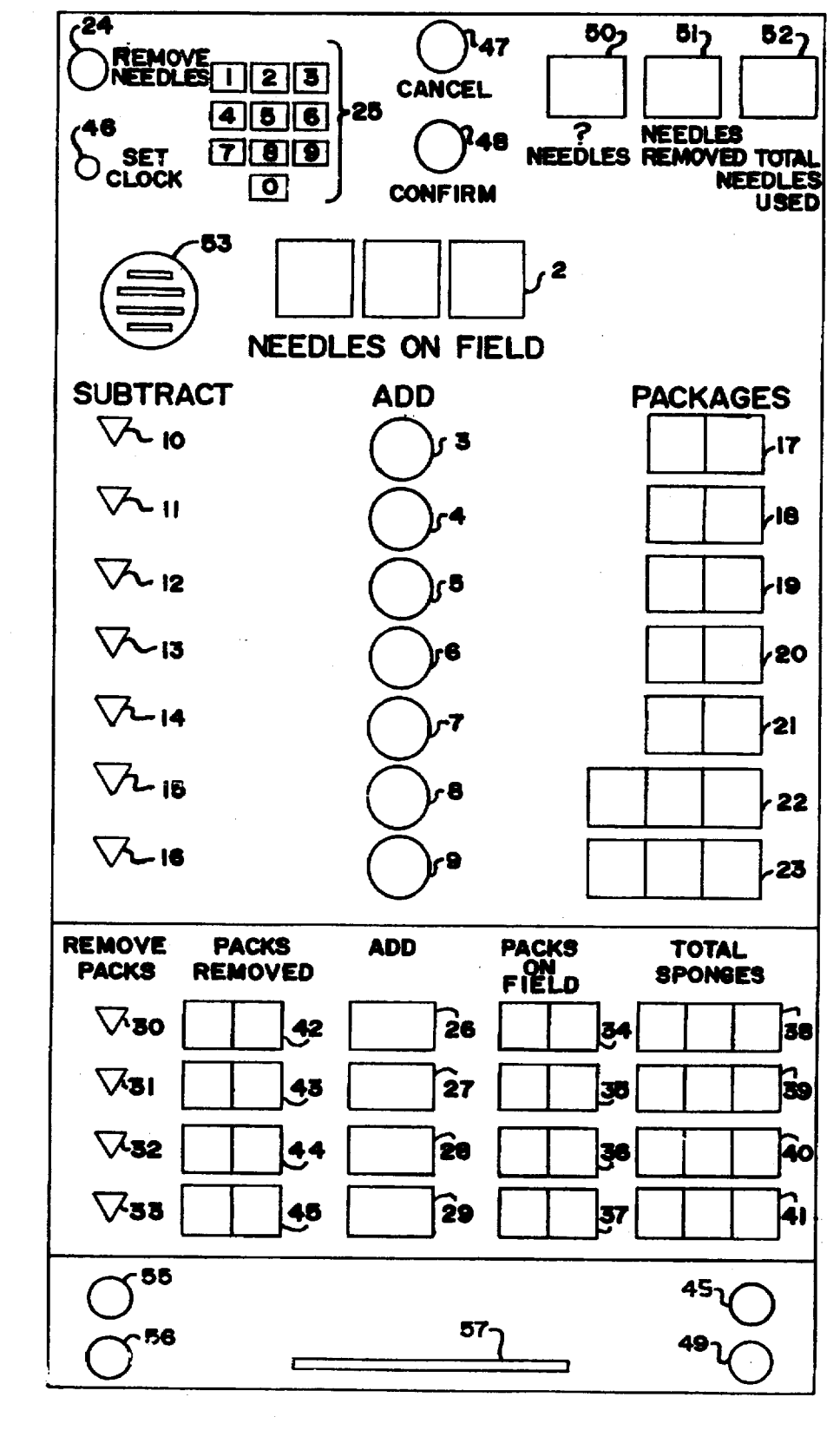
Figure 2:
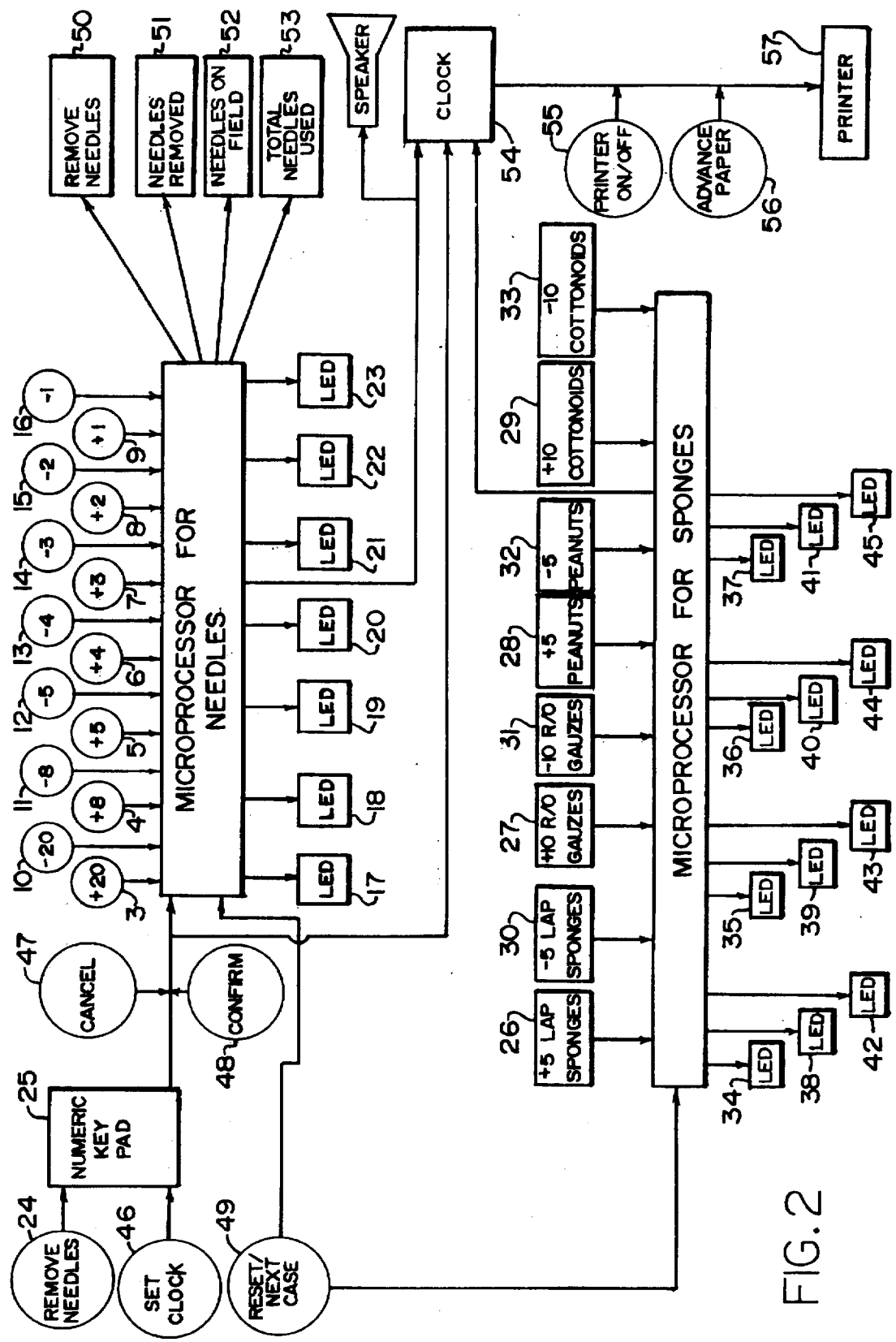
FIG. 2 Flow diagram of the counter

Referring to FIG. 1, the calculator consists of a rectangle box 1 consisting of four parts. The needle count portion shows a large three digit LED display (52) showing the total number of needles on the surgical field. (3), (4), (5), (6), (7), (8) and (9) are numbered push-buttons. The number on the button corresponds to the number of needles found in a typical package. (17), (18), (19), (20), (21), (22), (23) are LED displays showing the total number of those types of needle packages on the field.

The needle input buttons then provide a total tally of the number of needles ("total needles used") used in the procedure. This tally is displayed by a visual display means at 52 in the FIG. 1. The total number of packages of that type of needle appears as a visual display in readouts 17–23. Pressing (4), for example, will advance the count in (18) by one and the count in (52) by eight since that button corresponds to a single package of eight needles. Pressing (8) twice will advance (22) by two and (52) by four since that corresponds to a package of two needles. Of course, different counts may correspond to different buttons and the numbers given here are by example only.

Initially the "total needles used" in 52 will equal the "needles on field" shown as a visual display 2. As needles are removed from the patient they are put away from the operating area (the field) and are known as "needles removed." The total of such needles removed is input numerically by the remove needles keypad 25. The numerical value input is displayed in the "? needles" display 50. The nurse then confirms that this number is correct and the numercial value then appears in 51 (this display keeps a running total of total needles removed).

The buttons 3–9 provide a numerical value that corresponds to the number of needles in particular types of packages that are brought into the operating area. The number of such packages of each type is kept as a tally in display means 17–23 for each type of package. The total number of needles used is shown in 52 and is increased by the amount of needles in that package.

The number of "Total needles used" usually (see below) does not go down but "needles on the field" will then reflect the difference between total needles and needles removed. As needles are removed, then, the total needles used remains the same but needles on the field will go down. The number of "needles on the field" plus the numerical value of "needles removed" should always equal "total needles used." If the nurse makes a mistake on the keypad the cancel button 47 may be used to clear this number and start the subtraction again.

The subtract buttons 10–16 are input means and they correspond to the numbers of needles in packages that those buttons (3), (4), (5), (6), (7), (8), (9) correspond to and allow a like number of needles to be subtracted for each package that is removed. If an Add button is accidently pressed, that error can be corrected by pressing the Subtract button that corresponds to that package. Furthermore, if at the last minute the surgeon decides not to use that needle package, that package can be removed from the field and the count corrected by the subtract button. In this way, the subtract buttons can be used to decrese the total number of needles used on occasion when errors such as this occur.

Used suture needles are stored in boxes which have numbered arrays in foam or in a magnetic base. They may contain 40 or more needles. When the box is full the scrub technician and circulating nurse may decide to remove those needles from the field. The upper portion of the display contains features designed for this event.

A numeric keypad 25 allows the circulating nurse to remove any number of needles from the field. If forty needles are removed from the surgical field, (24) is pressed and "40" is entered through the numeric keypad (25). "40" appears in the display (50) and when "Confirm" (48) is pressed the figure in (52) decreases by 40, but the counts in displays (17) to (23) which represent numbers of packages, do not change. Pressing (47) "Cancel" before (48) is pressed will abort the process and return the display in (50) to "000". (53) shows the total number of needles used during surgery i.e. the sum of (52) and (51) i.e. the number of needles both currently in the field and those that have already been removed from the field.

The lower section accounts for sponges. The count for each class of sponges is separate. Unlike suture needles sponge counts are not commingled. (26) represents a package of 5 laparotomy sponges, (27) represents a package of 10 gauzes, (28) represents a package of 5 "peanuts", (29) represents a package of 10 "cottonoids".

For example, pressing (26) will advance the count in LED display (34) by one and the LED display (38) by five. (30), (31), (32), (33) are the subtraction buttons. They are pressed when soiled sponges, which have been bundled in the same number as in a new package (e.g. 5 laps, 10 gauzes, etc.) are removed by the circulating nurse. (42), (43), (44) and (45) are LED displays which show the number of packages of soiled laparotomy sponges, radio-opaque gauzes, "peanuts" and "cottonoids" respectively, which have been removed. They are colored green in contrast to the other LED displays which are red.

The bottom part of the invention consists of the printer. (57) which prints out the time each needle and sponge package is placed on the field. A clock (54) keeps time at which each package of needles has been entered into the calculator.

FIG. 3 gives a sample of the output of the printer. This shows a typical output record that would include each input as well as the time that occured. Keeping a record of such by time may be important as it may help the users. If a certain package of needles or sponges was entered at a certain time, there would be no misunderstanding or double counting between circulating nurses when there is a change of shift or when nurses relieve each other for short breaks. A speaker (53) provides the audible output when the function buttons are pressed.

The calculator may be fixed to a wall at eye level adjacent to a writing board. If suture needles and sponges packages have been stacked for the operation then the circulating nurse presses the button corresponding to the number of needles in the package once for each package.

As additional sponge and needle packages are used during surgery they are entered into the calculator. The buttons on the display may be colored differently and the number on it may be displayed prominently. If a button is pressed by mistake that error can be readily corrected by pressing the adjacent "subtract" button. The subtract buttons may be designed less prominently because routinely they are less likely to be used.

If, for instance, a needle box is full with forty-four needles then, after verifying the needle count with the scrub techician, the circulating nurse takes possesion of the box. The nurse presses (24) and then enters that number in display (50) by using the numeric keypad (25). (48) is pressed to confirm that forty four needles are to be removed from the field. The count in (52) will decrease by forty-four while in (51) will increase by forty-four. The displays in (17) to (23), which represent the number of needle packages, do not change.

When sponges are put on the surgical field the button corresponding to the sponge is depressed. For example, if three packages of laparotomy sponges are put on the field (26) is pressed three times. (34) will increase by three and (38) will increase by fifteen. Used sponges are bundled in the same quantity as in a new package before being removed by the circulating nurse. Accordingly, used laparotomy sponges are disposed of in bundles of five, 4"×4" radio-opaque gauzes in tens, "Peanuts" in fives and "Cottonoids" in tens.

When five laparotomy sponges have been counted and put aside (30) is pressed once. The count in (34) will decrease by one and the count in (38) will decrease by five. The count in LED (42) will increase by one. Display readouts 38–41 represent total sponges in use, i.e. on the operating field.

Unlike the needles, there is no separate display that shows total sponges or sponge packages used. (38), (39), (40) and (41) show total sponges used only if the corresponding subtract buttons (30), (31), (32) and (33) have not been pressed: (42), (43), (44), and (45) will be zero. As packages are removed buttons (30–33) are used to count each package that is removed and this decreases packages on field (34–37) by one package and also decreases total sponges by that number of sponges in that package for example: if 2 packages of laparotomy sponges are removed button (30) is pushed once and the count in (34) decreases by 1 and the count in (38) decreases by 5. When (31) is pressed, (43) will increase by one, (35) will decrease by one and (39) will decrease by ten. When (32) is pressed, (44) will increase by one, (36) will decrease by one and (40) will decrease by five. When (33) is pressed, (45) will increase by one, (37) will decrease by one and (41) will decrease by ten. Total laparotomy sponge packages used, i.e. removed and in the field during surgery equals (42) plus (34). Total gauze sponge packages used during surgery equals (43) plus (35). Total peanut sponge packages used during surgery equals (44) plus (36). Total cottonoid sponge packages used during surgery equals (45) plus (37). The color of LEDs (34), (35), (36) and (37), which represent sponge packages still on the field will be red, whereas the color of LEDs (42), (43), (44) and (45), which represent sponge packages removed from the field will be green. This contrast allows the scrub nurse and circulating nurse to see at a quick glance the disposition of the sponges.

After the case is finished the RESET/Next Case button (49) is pressed to return all the numbers in the displays to zero for the next case. The clock is programed by depressing (46) and after entering the date and time into display (50), it is set by pressing (48).

I claim:

1. A calculator for displaying the numbers of sponges and needles used during an operation, said calculator comprising:

an enclosure containing memory components therein, a visual display means for displaying a total needle numerical value and a total sponge numerical value and providing indicia on said calculator enclosure to designate said total sponge and said total needle numerical value;

a means for maintaining a total needle numerical value and a means for maintaining a numerical needle package count, a first push-activated means comprising a series of buttons for increasing both said total needle numerical value in increments of 5, 8 and 20 depending on a particular one of said series of buttons being pushed, and increasing said needle package count by 1 with each push, a second push activated means for inputting and displaying a numerical value of total needles removed; a means for calculating and displaying a numerical value of needles on the field, said value of needles on the field calculated as the difference of said value of total needle numerical value and said total needles removed;

a means for displaying and maintaining a total value of sponges by type and a numerical value of sponge packages by type, a third push-activated means comprising at least two buttons for increasing both said total sponge value by type in increments of 5 and 10 depending on a particular one of said buttons being pushed, and increasing said sponge package count by 1 with each push.

2. The apparatus of claim 1 having a fourth push activated means comprising a series of buttons for decreasing both said total needle numerical value in increments of 20, 8 and 5 depending on a particular one of said series of buttons being pushed, and decreasing said total package numerical value in increments of 1 with each push.

3. The apparatus of claim 2 having a fifth push activated means comprising a series of buttons for increasing both said total needle numerical value in increments of 4, 3, 2, and 1 depending on a particular one of said series of buttons being pushed, and increasing said needle package count by 1 corresponding with each push.

4. The apparatus of claim 3 having a sixth push activated means comprising a series of buttons for decreasing both said total needle numerical value in increments of 4, 3, 2, and 1 depending on a particular one of said series of buttons being pushed, and decreasing said total package numerical value in increments of 1.

5. The apparatus of claim 1 wherein said first and said second push activated means are color coded.

6. The apparatus of claim 1 having a means for keeping the time and maintaining a time record for each activation of said first and second push activation means and said time record including which of said first and second push activation means has been pushed.

7. The apparatus of claim 2 having a means for displaying a preliminary value of needles removed; a means for canceling said preliminary value of needles removed; and a means for both confirming said preliminary value of needles removed and adding said preliminary value to said total value of needles removed.

8. The apparatus of claim 3 having a means for displaying a preliminary value of needles removed; a means for canceling said preliminary value of needles removed; and a means for both confirming said preliminary value of needles removed and adding said preliminary value to said value of total needles removed.

9. The apparatus of claim 6 having a means for displaying a preliminary value of needles removed; a means for canceling said preliminary value of needles removed; and a means for both confirming said preliminary value of needles removed and adding said preliminary value to said value of total needles removed.

10. The apparatus of claim 7 having a means for displaying a preliminary value of needles removed; a means for canceling said preliminary value of needles removed; and a means for both confirming said preliminary value of needles removed and adding said preliminary value to said value of total needles removed.

11. The apparatus of claim 2 having a means to zero all of said numerical values and displays.

12. The apparatus of claim 3 having a means to zero all of said numerical values and displays.

13. The apparatus of claim 4 having a means to zero all of said numerical values and displays.

14. The apparatus of claim 2 a means for audible confirmation of the activation of said first and second push activated means.

* * * * *